United States Patent
Kumar et al.

(10) Patent No.: US 7,847,094 B2
(45) Date of Patent: Dec. 7, 2010

(54) INDUSTRIAL PREPARATION OF 11-[4-{2-(2-HYDROXYETHOXY) ETHYL}-1-PIPERAZINYL] DIBENZO [B,F]-[1,4]THIAZEPINE

(75) Inventors: Ashok Kumar, Maharashtra (IN); Dharmendra Singh, Maharashtra (IN); Swapnali Hemant Patil, Maharashtra (IN); Ganesh Devidas Mahale, Maharashtra (IN); Uttamrao Arjunrao Sawant, Maharashtra (IN); Balasaheb Ganpat Jadhav, Maharashtra (IN); Ragneshkumar Rana, Maharashtra (IN)

(73) Assignee: IPCA Laboratories Limited, Mumbai (IN)

( * ) Notice: Subject to any disclaimer, the term of this patent is extended or adjusted under 35 U.S.C. 154(b) by 713 days.

(21) Appl. No.: 11/808,360

(22) Filed: Jun. 8, 2007

(65) Prior Publication Data

US 2007/0293471 A1    Dec. 20, 2007

Related U.S. Application Data

(63) Continuation-in-part of application No. PCT/IN2005/000028, filed on Jan. 24, 2005.

(51) Int. Cl.
C07D 281/16    (2006.01)
(52) U.S. Cl. ....................................................... 540/551
(58) Field of Classification Search ................... 540/551
See application file for complete search history.

(56) References Cited

U.S. PATENT DOCUMENTS

| 4,879,288 A | 11/1989 | Warawa et al. |
| 2004/0220400 A1 | 11/2004 | Diller et al. |

FOREIGN PATENT DOCUMENTS

EP    0 282 236 A1    9/1988

*Primary Examiner*—Brenda L Coleman
(74) *Attorney, Agent, or Firm*—Blank Rome LLP

(57) ABSTRACT

Disclosed herein is an industrial preparation of Quetiapine by the reaction of 11-piperazinyldibenzo[b,f][1,4]-thiazepine or its salt with 2-(2-chloroethoxy)ethanol in presence of an organic or inorganic base under neat or aqueous condition to form 11-[4-{2-(2-hydroxyethoxy)ethyl}-1-piperazinyl] dibenzo[b,f]-[1,4]thiazepine. The quetiapine free base obtained is further converted to its hemi-fumarate salt.

16 Claims, No Drawings

INDUSTRIAL PREPARATION OF 11-[4-{2-(2-HYDROXYETHOXY) ETHYL}-1-PIPERAZINYL] DIBENZO [B,F]-[1,4]THIAZEPINE

This application is a continuation-in-part of PCT/IN2005/000028, filed Jan. 24, 2005, published as WO2006/077602, which is incorporated herein by reference.

FIELD OF INVENTION

The present invention refers to a novel process for the preparation of 11-[4-{2-(2-hydroxy-ethoxy)ethyl}-1-piperazinyl]dibenzo[b,f]-[1,4]thiazepine of Formula I, a known pharmaceutical agent for curing schizophrenia.

BACKGROUND OF THE INVENTION

11-[4-{2-(2-hydroxyethoxy) ethyl}-1-piperazinyl] dibenzo[b,f]-[1,4]thiazepine of the Formula I known under the international non-proprietary name quetiapine has anti-dopaminergic and/or serotonin receptor antagonist activity, and is used in the clinical practice as an anti-psychotic or neuroleptic agent especially in the treatment of Schizophrenia.

Quetiapine and its process for preparation is first disclosed in the patent specification EP0240228 and various other processes for the preparation are disclosed in EP0282236, WO0155125, WO9906381, WO2004076431.

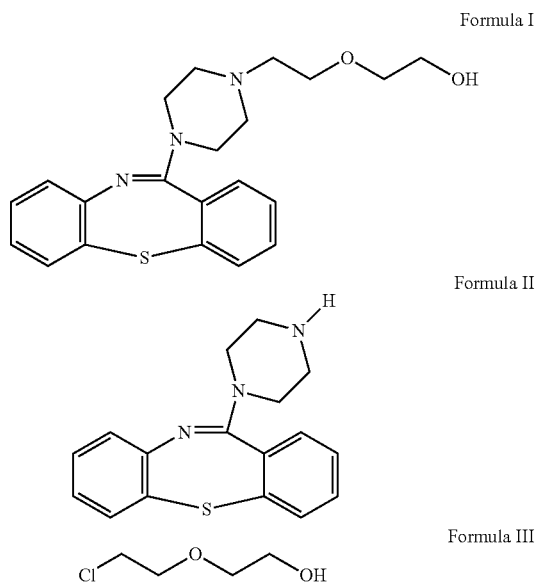

Formula I

Formula II

Formula III

In EP0240228, quetiapine was prepared by condensing a compound of Formula II (11-piperazinyldibenzo[b,f][1,4]-thiazepine) with 2-(2-chloroethoxy)ethanol of Formula III in polar organic solvents or aprotic organic solvents, e.g., N.N-dimethylformamide, N-methylpyrrolidone. Polar solvents exemplified were methanol, ethanol, isopropanol or hexanol or their isomers. Compound of Formula II may be employed in the reaction as its free base or its acid addition salt. An inorganic base like sodium carbonate or potassium carbonate was used in the reaction. The reaction was optionally carried out in the presence of promoter/catalyst such as sodium iodide also. The reaction times were reported to be 24 hours or more, but in practice even after 35 hours about 7 to 8% of starting 11-piperazinyldibenzo[b,f][1,4]-thiazepine has been found to be remained unreacted in the reaction. The reaction does not go up to completion, even if excess 2-(2-chloroethoxy)ethanol is used. This incomplete reaction necessitates further purification, incurring heavy losses of product and the purification is difficult due to similar properties of product and starting material 11-piperazinyldibenzo[b,f][1,4]-thiazepine.

A modification of EP0240228 was reported in WO2004076431 which deals with an attempt to reduce the reaction time and in this improved process the 11-piperazinyldibenzo[b,f][1,4]-thiazepine dihydrochloride was reacted with 2-(2-chloroethoxy)ethanol in an organic solvent in presence of a base and a phase transfer catalyst in order to complete reaction in a lesser time. According to the process disclosed in WO2004076431, after 4 hours of reaction unreacted 11-piperazinyldibenzo[b,f][1,4]-thiazepine was found to be about 9.7% (see Example 10). As per the details, the reaction completes only in 17 hours and the product in the reaction mass is only 95.5% and unreacted starting material was 1.1% to 0.26%. WO2004076431 also teaches the use of optional alkali metal halide as a promoter. '431 patent highlights the use of phase transfer catalyst (improved subject matter) for the completion of reaction and the yields reported are still on a lower side ranging from about 60 to 73% (see examples)

This indicates that there is a need for improvement in the process of making quetiapine wherein a complete reaction is achieved that too in much shorter time resulting in high yield and purity.

SUMMARY OF THE INVENTION

It is an objective of the present invention to overcome or ameliorate at least one of the disadvantages of the prior art or to provide a useful alternative.

It is an objective of the present invention, in its preferred form, to provide an industrial process for 11-[4-{2-(2-hydroxyethoxy) ethyl}-1-piperazinyl]dibenzo[b,f]-[1,4]thiazepine and its pharmaceutically acceptable salts wherein the complete reaction of 11-piperazinyldibenzo[b,f][1,4]-thiazepine and 2-(2-chloroethoxy)ethanol is achieved preferably in much shorter time leading to a product of higher quality in higher yield.

Accordingly, in the present invention, the compound of Formula II is reacted with the compound of Formula III in presence of a base (organic or inorganic) in an aqueous or neat condition to form 11-[4-{2-(2-hydroxyethoxy) ethyl}-1-piperazinyl]dibenzo[b,f]-[1,4]thiazepine.

In a preferred embodiment of the present invention, the compound of Formula II and compound of Formula III are treated in presence of a base in water as solvent at a temperature of about 100 to 105° C. for a period of about 4 to 9 hours during which the reaction is complete to the extent of 99.9% or more.

In yet another embodiment of the present invention the reaction is performed in water medium in presence of an alkali metal iodide such as sodium iodide or potassium iodide in catalytic amounts.

In another aspect, of the present invention, the compound of Formula II and compound of Formula III are reacted in presence of a base, preferably an organic base, and an alkali metal iodide in the absence of any solvent (i.e. neat condition) at a temperature of about 80 to 100° C. for a period of about 3 to 5 hours during which the reaction is complete to the extent of 99.9% or more. In this case, no solvent is used and the reactants are in emulsion/suspension state. "Solvent" as used herein include organic solvent and aqueous solvent.

In yet another aspect, the present invention relates to quetiapine hemi-fumarate (hereinafter also referred as quetiapine fumarate) made by the process of the present invention.

DETAILED DESCRIPTION OF THE PREFERRED EMBODIMENTS

This invention provides an improved industrial synthesis of quetiapine and its hemi-fumarate salt by the reaction of a compound of Formula II with a compound of Formula III in shorter duration of time with minimal impurity generation and almost complete transformation of compound of 11-piperazinyldibenzo[b,f][1,4]-thiazepine. The quetiapine free base obtained by the process of the present invention may be further converted to its hemi-fumarate salt.

It is now surprisingly found that the above reaction when carried out in a water medium—a green solvent, as against the prior teachings of organic solvents, both protic and aprotic, the reaction leads to completion with only traces of starting material (less than 0.1%) remaining. Another important feature of the present invention is the stability of both the reactants and product, the 11-[4-{2-(2-hydroxyethoxy) ethyl}-1-piperazinyl]dibenzo[b,f]-[1,4]thiazepine, in aqueous condition and the much faster rate of reaction which allows high conversion in shorter duration. The reaction is found to be reproducible in large scale.

In the process of the present invention, a mixture of the compound of Formula II, the compound of Formula III, and a basic substance (organic or an inorganic base) is heated in a medium of water at reflux temperature for a period of 4 to 8 hours. The ideal temperature of reaction is in the range of 100 to 105° C.

The compound of Formula II (11-piperazinyldibenzo[b,f][1,4]-thiazepine) can be used either as free base or its hydrochloride salt in the reaction. When an acid salt of compound of Formula II like hydrochloride salt is used in the reaction, an excess amount of base is used which is required to neutralize the hydrochloride salt to liberate free base in the reaction.

In another aspect, the reaction of compound of Formula II with 2-(2-chloroethoxy)ethanol can be completed in much shorter time when the reaction is performed in the absence of a solvent and in the presence of an organic base. The use of an organic base in this transformation is not referred in any of the prior art. In a preferred process, an alkali metal iodide is used in the reaction as a promoter. This neat reaction of compound of Formula II with 2-(2-chloroethoxy)ethanol in the presence of an organic base is carried out by mixing and heating the components at about 80 to 100° C. for a period of 3 to 5 hours, after which the starting compound of Formula II is almost absent (less than 0.05% by HPLC analysis) in the reaction mass (the compound of Formula II is almost completely consumed by the reaction).

The basic substance may be an organic or inorganic base. The inorganic base used in the present invention may be any known inorganic base, such as sodium carbonate, sodium bicarbonate, or potassium carbonate. The selection of a particular base is not critical for the success of the reaction. The inorganic base is preferably used in molar amounts of about 1 to 6 moles relative to the compound of Formula II.

The organic base used in the reaction is selected from trialkyl amines such as triethyl amine, trimethyl amine, diisopropyl amine etc., or dialkyl anilines such as dimethyl aniline or dimethylaminopyridine or -methyl morpholine or the like. The organic base used is preferably in molar amounts of about 1 to 3 moles relative to the starting compound of Formula II.

The 2-(2-chloroethoxy)ethanol (Formula III) is preferably used in a molar amount ranging from about 1 to 1.5 molar equivalents relative to compound of Formula II. For reasons of economy of the process, higher amounts of the reagent, 2-(2-chloroethoxy)ethanol, are not used. The volume of solvent used in the aqueous reaction is preferably in the range of 2 to 4 volume with respect to the starting compound of Formula II. Higher volumes of water can also be used but concentrated reaction medium is preferred for operating in large scale.

In a preferred embodiment of the reaction, an alkali metal iodide, such as sodium iodide or potassium iodide, is used as a promoting agent along with the mixture of compounds of Formula II and Formula III and base in an aqueous medium.

In an optional feature of the invention, a phase transfer catalyst may be used along with the reactants of Formula II and Formula III, base, and sodium iodide in an aqueous medium. When a phase transfer catalyst (PTC) is used in present process, the reaction time is further reduced to about 3 to 6 hours in place of 4 to 9 hours without PTC. It is, however, observed that other than reduction of reaction time by 1 to 2 hours no other significant advantages are achieved in terms of purity or yield of product, i.e., the 11-[4-{2-(2-hydroxyethoxy) ethyl}-1-piperazinyl]dibenzo[b,f]-[1,4]thiazepine, when a phase transfer catalyst is used. The phase transfer catalyst of choice is tertrabutyl ammonium halide and preferably tertrabutyl ammonium bromide.

The quetiapine free base formed in the reaction is isolated as an oily mass by the steps of extracting the product using an organic solvent selected from hydrocarbon solvents like toluene, xylene, heptane or chlorinated hydrocarbon solvent such as methylene chloride, and removing the organic solvent by distillation, preferably under reduced pressure.

The isolated crude quetiapine free base is further converted directly to the hemi-fumarate salt without subjecting to additional purification by suspending the oily mass in ethanol and combining it with fumaric acid in 0.55 to 1.0 molar equivalents relative to free base. The ethanol solution is cooled to precipitate the quetiapine hemi-fumarate in an yield of about 75 to 80%. The purity of quetiapine hemifumarate so obtained is at least 99.5%.

Apart from greening of the process the drastic yield and purity improvement caused by the above described variations can lead to an efficient and commercially acceptable synthetic process for the preparation of quetiapine hemi-fumarate.

The starting material 11-piperazinyldibenzo[b,f][1,4]-thiazepine (II) was prepared according to the process disclosed in U.S. Pat. No. 3,539,573, which is incorporated herein by reference.

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in this example.

EXAMPLE 1

In a reaction vessel, a mixture of 11-piperazinyldibenzo[b,f][1,4]-thiazepine (10 Kg), 2-(2-chloroethoxy)ethanol (6.33 kg), sodium carbonate (21.55 kg) and 0.2 kg sodium iodide was heated in 30 liters of water to about 100° C. The reaction mixture was maintained at about 100 to 105° C. for about 7 hours. The starting 11-piperazinyldibenzo[b,f][1,4]-thiazepine was about 0.26% by HPLC. Maintained for another 2 hours till the 11-piperazinyldibenzo[b,f][1,4]-thiazepine was about less than 0.1% by HPLC analysis. The reaction mass was cooled to about 30° C. and aqueous layer extracted with methylenedichloride (100 liters). The organic layer was washed with water and concentrated under reduced pressure. The oily residue was so obtained was suspended in 100 liters of ethanol (commercial) and 4.1 kg fumaric acid was added. The mixture is stirred for about 6 hours and cooled to about 10° C. The precipitated quetiapine hemi-fumarate salt was filtered and dried to give 12 Kg (yield 80%, purity 99.6% by HPLC analysis).

EXAMPLE 2

In a reaction vessel, a mixture of 11-piperazinyldibenzo[b,f][1,4]-thiazepine (10 Kg), 2-(2-chloroethoxy)ethanol (6.33 kg), sodium carbonate (21.55 kg), 1 kg tetrabutyl ammonium bromide and 0.2 kg sodium iodide was heated in 30 liters of water to about 100° C. The reaction mixture was maintained at about 100° to 105° C. for about 5 hours. Starting 11-piperazinyldibenzo[b,f][1,4]-thiazepine was about 0.3% by HPLC. Maintained for another 2 hours till the 11-piperazinyldibenzo[b,f][1,4]-thiazepine was about less than 0.08% by HPLC analysis. The reaction mass was cooled to about 30° C. and aqueous layer extracted with methylenedichloride (100 liters). The organic layer was washed with water and concentrated under reduced pressure. The oily residue was so obtained was suspended in 100 litres of ethanol (commercial) and 4.1 kg fumaric acid was added. The mixture is stirred for about 4 hours and cooled to about 10° C. The precipitated quetiapine hemi-fumarate salt was filtered and dried to give 12 Kg (yield 80% & purity 99.8% by HPLC analysis)

EXAMPLE 3

In a reaction vessel, a mixture of 11-piperazinyldibenzo[b,f][1,4]-thiazepine dihydrochloride (10 Kg), 2-(2-chloroethoxy)ethanol (5.1 kg), sodium carbonate (17.3 kg) and 0.16 kg sodium iodide was heated in 30 liters of water to about 100° C. The reaction mixture was maintained at about 100° to 105° C. for about 7 hours. Starting 11-piperazinyldibenzo[b,f][1,4]-thiazepine was about 0.25% by HPLC. Maintained for another 2 hours till 11-piperazinyldibenzo[b,f][1,4]-thiazepine was about less than 0.1% by HPLC analysis. The reaction mass was cooled to about 30° C. and aqueous layer extracted with methylenedichloride. The organic layer was washed with water and concentrated under reduced pressure. The oily residue was so obtained was suspended in 100 litres of ethanol (commercial) and 3.3 kg fumaric acid was added. The mixture is stirred for about 6 hours and cooled to about 15° C. The precipitated quetiapine hemi-fumarate salt was filtered and dried to give 9.6 Kg (yield 80% & purity 99.5% by HPLC analysis).

EXAMPLE 4

In a reaction vessel, a mixture of 11-piperazinyldibenzo[b,f][1,4]-thiazepine (10 Kg), 2-(2-chloroethoxy)ethanol (6.3 kg), 5.4 kg triethyl amine and 0.2 kg sodium iodide was heated under mixing to about 85° C. The reaction mixture was maintained at about 80° to 85° C. for about 3 hours. Starting 11-piperazinyldibenzo[b,f][1,4]-thiazepine was about 0.1% by HPLC. Maintained for another 2 hours till 11-piperazinyldibenzo[b,f][1,4]-thiazepine was about less than 0.05% by HPLC analysis. The reaction mass was cooled to about 30° C. and added 40 litres of water and aqueous layer extracted with methylene chloride. The organic layer was washed with water and concentrated under reduced pressure. The oily residue was so obtained suspended in 100 litres of ethanol (commercial) and 3.3 kg fumaric acid was added. The mixture was stirred for about 6 hours and cooled to about 15° C. The precipitated quetiapine hemi-fumarate salt was filtered and dried to give 12 Kg (yield 80% and purity 99.8% by HPLC analysis).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:
1. A process for preparing quetiapine of Formula I

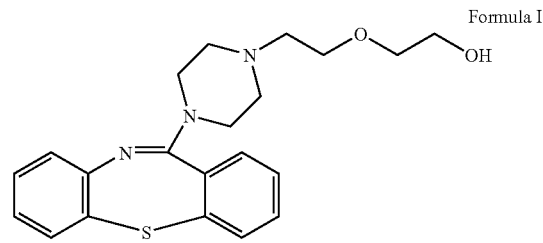

Formula I comprising the steps of
   a) heating a mixture containing the compound of Formula II Formula II the compound of Formula III Formula III and a base, in an aqueous medium or absence of a solvent; and
   b) isolating the quetiapine from said mixture.
2. The process of claim 1, wherein the base is an inorganic base.
3. The process of claim 2, wherein the inorganic base is selected from the group of sodium carbonate, sodium bicarbonate, and potassium carbonate.
4. The process of claim 1, wherein the base is an organic base.
5. The process of claim 4, wherein the organic base is selected from the group consisting of trialkyl amines, dialkyl anilines, and dialkyl amino pyridines.

6. The process of claim 1, wherein the step a) is performed in the presence of an alkali metal iodide.

7. The process of claim 6, wherein the alkali metal iodide is sodium iodide or potassium iodide.

8. The process of claim 1, wherein step a) is performed in the presence of a phase transfer catalyst.

9. The process of claim 8, wherein the phase transfer catalyst is tetrabutylammonium bromide.

10. The process of claim 1, wherein the aqueous medium is water.

11. The process of claim 10, wherein the volume of water used is about 2 to 4 volume/weight relative to the compound of Formula II.

12. The process of claim 1, wherein the reaction temperature of step a) is about 100 to 105° C.

13. The process of claim 1, wherein step b) is accomplished by extraction using an organic solvent.

14. The process of claim 13, wherein the organic solvent is selected from hydrocarbon solvents or chlorinated hydrocarbon solvents.

15. The process of claim 14, wherein the organic solvent is toluene or methylenedichloride.

16. The process of claim 1, further comprising the step of converting the quetiapine to quetiapine hemi-fumarate.

* * * * *